United States Patent [19]

Nash et al.

[11] Patent Number: 5,312,435
[45] Date of Patent: May 17, 1994

[54] FAIL PREDICTABLE, REINFORCED ANCHOR FOR HEMOSTATIC PUNCTURE CLOSURE

[75] Inventors: John Nash, Dowingtown; Douglas Evans, Devon, both of Pa.

[73] Assignee: Kensey Nash Corporation, Exton, Pa.

[21] Appl. No.: 64,192

[22] Filed: May 17, 1993

[51] Int. Cl.⁵ .............................................. A61B 17/04
[52] U.S. Cl. .................................. 606/213; 606/215; 604/15
[58] Field of Search ............... 606/213, 139, 215, 216, 606/228–232; 604/15

[56] References Cited

U.S. PATENT DOCUMENTS

| | | | |
|---|---|---|---|
| 4,743,257 | 5/1988 | Törmälä et al. | 623/16 |
| 4,744,364 | 5/1988 | Kensey | 606/213 |
| 5,041,129 | 8/1991 | Hayhurst et al. | 606/139 X |
| 5,053,046 | 10/1991 | Janese | 606/213 X |
| 5,061,274 | 10/1991 | Kensey | 606/213 X |
| 5,108,420 | 4/1992 | Marks | 606/213 |
| 5,108,421 | 4/1992 | Fowler | 606/215 X |
| 5,192,302 | 3/1993 | Kensey et al. | 606/215 X |

Primary Examiner—Peter A. Aschenbrenner
Attorney, Agent, or Firm—Caesar, Revise, Bernstein, Cohen & Pokotilow, Ltd.

[57] ABSTRACT

A closure for sealing a percutaneous puncture in an vessel, e.g., an artery, or lumen. The puncture also includes a puncture tract in which a portion of the closure is to be located. The closure comprises an elongated rigid anchor member formed of a resorbable material, a sealing member formed of a resorbable material, e.g., compressed collagen plug, and a thin resorbable material filament, e.g., a suture, connecting the anchor member and the sealing member. The anchor member is located in the interior of the vessel, with the sealing member being located in the puncture tract. An elongated reinforcing filament or ribbon, formed of a resorbable material, is incorporated in the elongated anchor member to prevent any portion of it from breaking away in the event that the anchor is loaded beyond its breaking point.

16 Claims, 1 Drawing Sheet

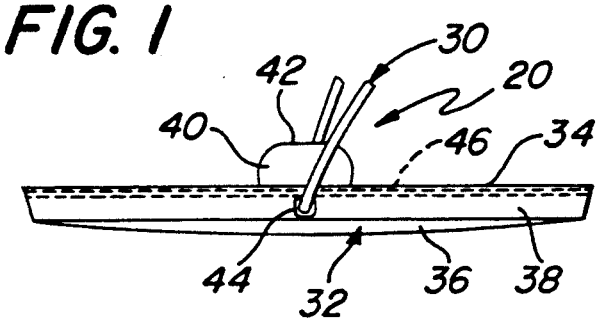
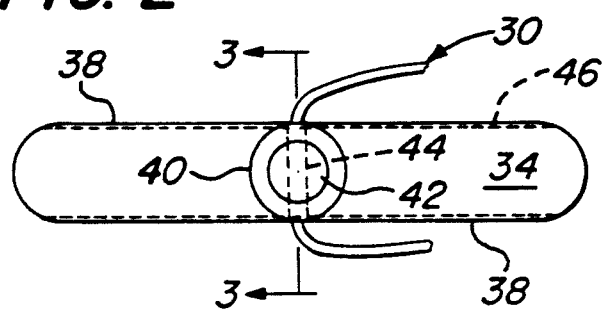
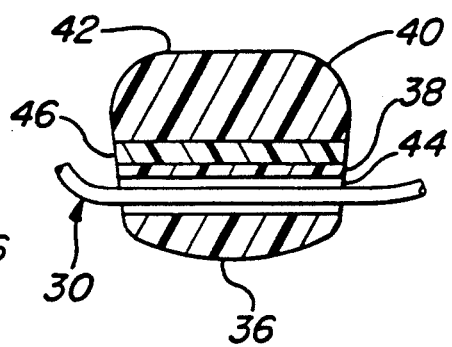
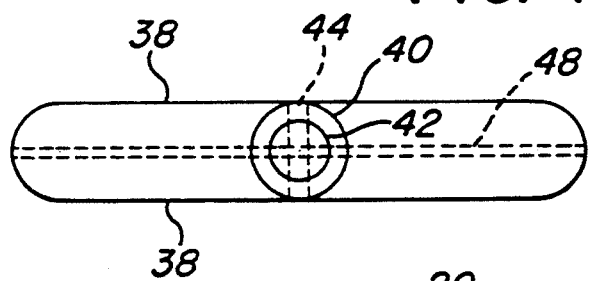
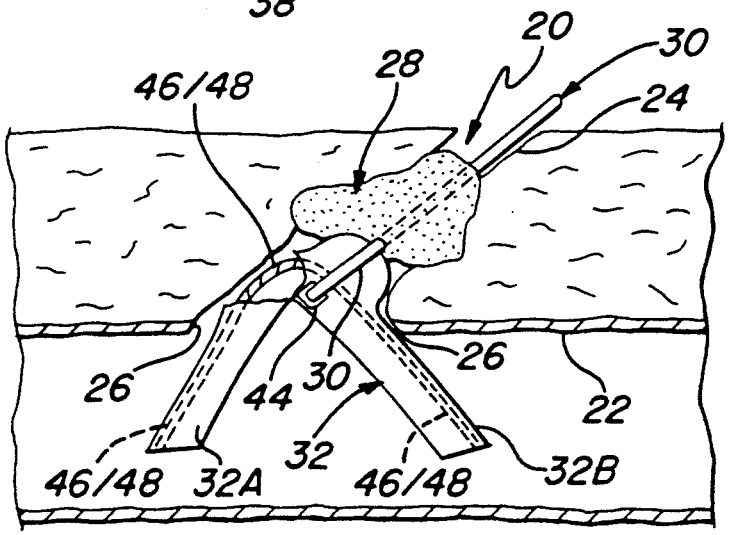

FAIL PREDICTABLE, REINFORCED ANCHOR FOR HEMOSTATIC PUNCTURE CLOSURE

BACKGROUND OF THE INVENTION

In a copending U.S. patent application Ser. No. 07/846,322, filed on Mar. 5, 1992, entitled Hemostatic Puncture Closure System and Method of Use, which is a Continuation-In-Part of a copending United States patent application Ser. No. 07/798,704, filed on Nov. 8, 1991, and of the same title, both of which are assigned to the same assignee as this invention, and whose disclosures are incorporated by reference herein, there are disclosed systems for sealing a percutaneous incision or puncture in a blood vessel. Those systems basically comprise a closure, an introducer, and a deployment instrument including a carrier for the closure.

The closure has three basic components, namely, a sealing member, an intraarterial anchor member, and a positioning member. The sealing member is in the form of an elongated rod-like plug, e.g., a compressed hemostatic, resorbable collagen sponge or foam. This plug member is arranged for sealing the puncture. The anchor member is an elongated, stiff, low-profile member which is arranged to be seated inside the artery against the artery wall contiguous with the puncture. The anchor member is molded of non-hemostatic resorbable polymer similar to resorbable suture. The positioning member comprises a filament, e.g., a resorbable suture. The filament connects the anchor member and the collagen plug (sealing member) via a pulley-like arrangement which serves to move the plug toward the anchor member by pulling on the filament when that member is located within the interior of the artery and in engagement with the inner wall of the artery contiguous with the incision or puncture. A tamping member, forming a portion of the deployment instrument is provided to tamp the plug within the puncture tract. This action causes the plug to deform into a larger diameter body. Expansion of the plug is enhanced by the fact that it is formed of a compressed collagen so that it expands in the presence of blood within the puncture tract. The expansion of the plug within the puncture tract serves to hold it in place. The closure quickly becomes locked in place through the clotting of the hemostatic collagen plug within the puncture tract, and by tension applied to the filament via spring means forming a portion of the deployment system.

In another copending U.S. patent application Ser. No. 08/012,816, filed on Feb. 3, 1993, entitled A Hemostatic Vessel Puncture Closure System Utilizing A Plug Located Within The Puncture Tract Spaced From The Vessel, And Method of Use, which is assigned to the same assignee as this invention, and whose disclosure is incorporated by reference herein, there is disclosed a system for sealing a percutaneous incision or puncture in a blood vessel or other lumen. That system includes a closure, similar in most respects to the closures disclosed in the above mentioned copending application but also having means for preventing the sealing portion of the closure from gaining access into the interior of the artery. In particular, the application Ser. No. 08/012,816 discloses a closure including a spacer member interposed between the anchor member and the plug member to keep the plug member in the puncture tract but spaced from the opening in the artery.

In some cases during deployment of a closure having an anchor like those of the above described systems, the anchor may break apart due to a material defect or a fault in the molding of the anchor. Such action may result in a portion of the anchor member becoming dislodged and being carried by the blood to some remote location within the patient's body, thereby posing a medical hazard.

The reinforcement of resorbable devices to increase their strength has been disclosed in U.S. Letters Pat. No. 4,743,257 (Tormala et al.). In particular that patent discloses surgical osteosynthesis devices or their component plates, pins, nails, medullary rods, screws, or corresponding structures formed of a resorbable polymer or copolymer matrix reinforced with resorbable reinforcement units of the same chemical element percentage composition as the matrix itself to increase the strength of the devices. There is no disclosure nor suggestion of some reinforcement means to hold pieces of an anchor of an arterial closure together should to prevent it from break apart and separating from other parts of the closure during a deployment operation.

Accordingly, the need exists for a vascular closure device having an anchor which is reinforced to preclude it from accidentally breaking apart and separating from the rest of the closure during its deployment or thereafter. A need also exists for a vascular closure including an anchor which is sufficiently reinforced so that if during the closure deployment procedure the physician is not satisfied with the placement of the anchor within the vessel and he/she decides to remove it, such action can be accomplished by pulling on the filament to cause the anchor to deform so that it can pass back out through the incision or puncture without any portion breaking away from the closure.

OBJECTS OF THE INVENTION

Accordingly, it is a general object of this invention to provide a device and methods of use which addresses the aforementioned needs of the prior art.

It is a further object of this invention to provide a vascular closure for safely and effectively sealing a percutaneous puncture or incision in a blood vessel within the body of a living being.

It is a further object of this invention to provide a vascular incision or puncture closure having a reinforced anchor.

SUMMARY OF THE INVENTION

These and other objects of this invention are achieved by providing a closure for sealing a percutaneous puncture in a blood vessel. The puncture comprises a tract extending through tissue overlying the vessel. The closure comprises anchoring means, sealing means, and filament means coupled to the anchoring means and the sealing means. The closure is arranged to be inserted into the puncture tract and through the puncture so that the anchoring means is within the artery and the sealing means is located in the puncture tract outside of the artery.

The anchoring means comprises a generally elongated member formed of a resorbable material having reinforcing means, e.g., a filament, ribbon or mesh also formed of a resorbable material, extending along substantially the length thereof and fixedly secured thereto, e.g., molded in situ therein, to prevent the anchoring member from breaking apart and separating from the closure.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 1 is a side elevational view of one embodiment of a reinforced anchor member, and an associated portion of the filament member, of a closure of this invention;

FIG. 2, is a top plan view of the anchor member and a portion of the filament member of the closure shown in FIG. 1;

FIG. 3 is an enlarged sectional view taken along line 3—3 of FIG. 2;

FIG. 4 is a top plan view of an alternative embodiment of an anchor member of the closure of this invention; and FIG. 5 is an enlarged illustration showing the closure of FIG. 1 being removed from a percutaneous puncture in an artery after it's anchor portion has been broken.

DETAILED DESCRIPTION OF THE PREFERRED EMBODIMENT

Referring now in greater detail to the various figures of the drawings wherein like reference characters refer to like parts, there is shown at 20 in FIG. 1 a portion of a closure device constructed in accordance with this invention, to seal a percutaneous puncture within a blood vessel 22, e.g., the femoral artery (FIG. 5). The puncture includes the tract 24 through the skin and underlying tissue leading up to the opening 26 in the wall of the vessel 22.

The closure device 20 is constructed in accordance with the teachings of the aforementioned patent applications, except for its anchor member (to be described later). Since this application incorporates by reference the details of the structure and operation of the closure and its deployment system of those applications, in the interest of brevity those details will not be reiterated herein. However, to expedite understanding of the invention a general overview of the closure 20 and the system for deploying it will now be given.

The closure 20 basically comprises a sealing member 28 (FIG. 5), a positioning member or filament 30, e.g., a resorbable suture (FIGS. 1, 2, 3, and 5), and an anchor member 32 (FIGS. 1-5). The sealing member 28 preferably comprises a compressed collagen or other hydrophilic resorbable material plug which is arranged to expand automatically in the presence of blood when it is located within the puncture tract. The filament 30, is a flexible member formed of a strong resorbable material, e.g., a resorbable suture. The anchor member 32 is an elongated member having a top surface (to be described later) including a domed projection (also to be described later) is the center thereof. A passageway (also to be described later) extends through the anchor member below the domed projection. The filament 30 extends through the passageway to connect the anchor member and the sealing member together in a pulley-like arrangement.

The closure is deployed by utilizing a deployment instrument (not shown) and a conventional introducer (not shown). The introducer basically comprises a tubular sheath having a distal free end insertable into the puncture tract and through the contiguous opening in the blood vessel wall. The deployment instrument includes a carrier for holding the closure therein. The carrier is insertable through the introducer sheath into the interior of the blood vessel and includes means to expel the anchor member therefrom.

The deployment instrument is retracted with respect to the introducer sheath after the anchoring member has been expelled from the instrument's carrier into the blood vessel, so that when the instrument is retracted it draws the anchor member into engagement with the distal free end of the introducer sheath. The introducer sheath and the deployment instrument are then withdrawn together to draw the anchor member, which is in engagement with the distal end of the introducer sheath, into engagement with the interior tissue of the vessel generally adjacent the opening in the wall thereof, whereupon the anchor catches on that tissue. Continued withdrawal of the instrument and introducer causes the pulley-like configuration of the filament to pull the collagen plug 28 toward the anchor member 32, thereby depositing the plug member in the puncture tract 24. The pulling on the filament 30 to bring the plug 28 into the puncture tract also has the effect of deforming the plug into a larger diameter body to aid in holding it in place therein. Moreover, since the plug is formed of a compressed collagen it also expands automatically in the presence of blood within the puncture tract, thereby further contributing to the plug's enlargement.

The deployment instrument also includes a tamper (not shown) which is mounted on the filament 30 and which is slidable thereon. The deployment of the plug member 28 also effects the deployment of the tamper into the puncture tract 24 proximally of the plug member. The tamper is then used to gently compress and lock the collagen plug in the puncture tract. The closure 20 is now locked in place through the clotting of the hemostatic collagen plug 28 and by tension on the filament 30 which is applied by a spring member (not shown) also forming a portion of the deployment system. Within a few hours after deployment, the anchor member 32 will be coated with fibrin and thus attached firmly to the arterial wall, thereby eliminating the possibility of distal embolization. After approximately thirty days, only a small deposit of anchor material will remain. In fact, resorption of all components making up the closure will have occurred after approximately sixty days. The anchor member is non-hemostatic and is sized to be hemodynamically insignificant in comparison to the size of the artery. Thus, the resorbable anchor has an insignificant hemodynamic effect on blood flow.

If the closure 20 is constructed in accordance with the teachings of application Ser. No. 08/012,816, so that it includes a spacer member (not shown) located between the distal end of the collagen sealing member 28 and the anchor member 32, when the filament is pulled to move the sealing member toward the anchor member, the sealing member engages the proximal (top) end of the spacer member. The spacer member, in turn, engages the domed portion of the anchor member which extends through the puncture so that the collagen sealing member is spaced from the opening in the artery wall in order to prevent any portion of the collagen plug from gaining ingress into the interior of the artery where it could flow distally.

Referring now to FIGS. 1-3 the details of the anchor member embodiment 32 will now be described. As can be seen that member basically comprises a thin, narrow, strip or bar of resorbable material which is sufficiently rigid such that once it is in position within the artery it is resistant to deformation to preclude it from bending to pass back through the puncture in the artery through which it was first introduced. One particularly effective material for the anchor member is a 50—50 mixture of polyglycolide (polyglycolic acid) and polylactide (polylactic acid) polymers sold by Medisorb Technologies International L. P. of Cincinnati, Ohio, and by Birmingham Polymers, Inc. of Birmingham, Ala. Other resorbable materials can be used, such as gelatin, polydioxanone, polyglyconate, and a resorbable elastomeric hydrogel that is a segmented block polymer of variable proportions of soft polyethylene oxide (PEO) and hard polybutylene terephathalate (PBT) segments sold by Osteotech, Inc. of Shrewsbury, N.J. under the trademark POLYACTIVE.

The anchor member 32 has a generally planar top surface 34, a radially contoured bottom surface 36 (FIGS. 1 and 3) and a peripheral side surface 38. Each end of the member 32 is rounded. The side surface 38 of the anchor member 32 tapers inward slightly from its top surface 34 to its bottom surface 36 as shown in FIGS. 1 and 3 to facilitate the removal of the plug from the mold for making it. A hemispherical dome-like projection 40 is located at the center of the top surface 34. The top surface 42 of the projection 40 is slightly flat. The dome-like projection 40 is arranged to extend into the opening 26 in the blood vessel wall when the anchor member 34 is properly deployed within that vessel.

A passageway 44 of generally square profile and rounded corners extends transversely across the member 32 below the projection 40 and close to the bottom surface 36. The filament 32 is threaded through the passageway 44 as shown clearly in FIGS. 1-3 to connect the plug member 28 to the anchor member 32 in the pulley-like arrangement.

In order to ensure that no portion of the anchor member can break off and separate from the closure 20 when the anchor member 32 is deployed within the blood vessel, the anchor member includes a flexible strip of resorbable reinforcing material extending along the length of the elongated portion of the anchor and fixedly secured thereto. That strip may take various forms. For example, in the embodiment of the anchor member shown in FIGS. 1-3, the strip comprises a ribbon 46. The width and length of the ribbon 46 is substantially the same as the width and length, respectively, of the anchor member itself and its ends are curved so that its periphery is substantially the same as the periphery of the top surface 34 of the anchor member. The ribbon 46 may be formed of an unapertured web of material or a woven or knitted mesh. In the embodiment of the anchor member shown in FIG. 4, the strip making up its reinforcement comprises a thin filament 48 whose length is substantially the same as that of the anchor member. The filament 48 may comprise a single strand (i.e., be a monofilament) or multiple strands (i.e., be a multifilament, e.g., a braid) and extends along the major central axis of the anchor member.

In the embodiment of the anchor member of FIGS. 1-3 the reinforcing ribbon 46 is molded in situ within the elongated portion of the anchor member just under its top surface 34 and above the transversely extending passageway 44. In the embodiment of the anchor member of FIG. 4 the reinforcing filament 48 is molded in situ within the elongated portion of the anchor member just under its top surface 34 and above the transversely extending passageway 44.

In all embodiments the flexible material making up the strip has greater tensile strength than the material making up the anchor portion itself. That factor, coupled with the flexibility of the strip, ensures that if anchor portion should fracture or otherwise break when positioned within the interior of the blood vessel, the various portions of the anchor will be held together by the flexible reinforcing strip so that no portion of the anchor member can break off and flow distally in the blood stream.

Moreover, since the reinforcing strip of each embodiment of the anchor member of this invention is located above the passageway 44 through which the filament 30 extends, if the anchor member should be fractured the entire closure can be readily removed from within the patient's body. This action is shown clearly in FIG. 5. In particular, if the anchor should become fractured, such as could occur during deployment or after deployment, whereupon it is in plural, e.g., two pieces 32A and 32B, the strip 46 or 48 will hold the pieces together and as a unit with the rest of the components making up the closure 20. All that the physician has to do to remove the closure is to pull on the proximal end of the filament 30 extending out of the puncture tract. This action causes the looped portion of the filament 30 extending through the passageway 44 under the reinforcing strip 46 or 48 to lift and pivot or "jack-knife" the portions 32A and 32B towards each other, so that they can pass through the opening 26 in the vessel wall and into the contiguous puncture tract 24. Continued pulling on the filament 30 will draw the closure out of the puncture tract.

Thus, it should be appreciated by those skilled in the art that the reinforcing means of the subject invention not only serves to prevent the breaking away of any portion of the anchor member 34, but also serves as means for enabling the easy and safe removal of the entire closure 20 from the patient's body. This latter factor is of considerable importance from at least two standpoints. Firstly, it enables the physician to remove a closure whose anchor member fractures during the deployment procedure. Secondly, it enables the physician to effect the removal of the closure from the patient's body in the event that the anchor member is not positioned as desired within the blood vessel, even though the anchor member has not broken or fractured. In this regard should the physician deem the anchor member to be undesirably positioned within the blood vessel, so that removal of the closure is indicated, all that the physician has to do is to pull firmly on the proximally extending portion of the filament 30 to cause the anchor member to deform plastically and then break as it tries to pass through the opening 26 in the blood vessel wall. Thus, one end or leg, e.g., 30A, of the anchor member will break from the remaining portion 30B. When this occurs the broken pieces 30A and 30B of the anchor member pivot with respect to each other, while being held together by the reinforcing strip, as described above. Accordingly, upon continued pulling on the filament 30 the broken anchor member will pass through the opening 26, into to contiguous puncture tract 24, and out of the patient's body.

One particularly effective material for the reinforcing strip 46 or 48 of this invention is polyglycolide (polyglycolic acid) such as sold by Medisorb Technologies International L. P. of Cincinnati, Ohio, and by Birmingham Polymers, Inc. of Birmingham, Ala. Where the strip is in the form of a filament, it may be a 3-0 polyglycolide resorbable suture, such as that sold under the trademark DEXON S by Davis & Geck a division of American Cyanamid Company. Other resorbable materials can be used to make up the reinforcing strip 46 or 48, such as polylactide (polylactic acid), a mixture of polyglycolide (polyglycolic acid) and polylactide (polylactic acid), POLYACTIVE resorbable elastomeric hydrogel, oxidized regenerated cellulose (e.g., a woven mesh sold by Johnson & Johnson under the trademark SURGICEL), polydioxanone, collagen (chromic gut suture), and polyglyconate, provided that they exhibit higher tensile strength than the material(s) making up the anchor member itself.

Without further elaboration the foregoing will so fully illustrate our invention that others may, by applying current or future knowledge, adopt the same for use under various conditions of service.

What is claimed is:

1. A closure for sealing a percutaneous puncture in a vessel or lumen of a living being, said puncture comprising a tract extending through tissue overlying the vessel, said closure comprises anchoring means, sealing means, and filament means, said closure being arranged to be inserted into the puncture tract and through the puncture in said vessel or lumen so that said anchoring means is within said vessel or lumen, said sealing means is within said puncture tract, and said filament means connecting said anchoring means and said sealing means, said anchoring means being a generally elongated member formed of a first resorbable material and including reinforcing means of a second resorbable material which has a higher tensile strength than said first material, said reinforcing means extending along substantially the length of said anchoring means and fixedly secured thereto to prevent said anchoring means from breaking apart and separating from said closure.

2. The closure of claim 1 wherein said reinforcing means is flexible.

3. The closure of claim 1 wherein said reinforcing means comprises a filament.

4. The closure of claim 3 wherein said filament comprises a suture.

5. The closure of claim 1 wherein said reinforcing means comprises a ribbon.

6. The closure of claim 1 wherein said reinforcing means comprises a mesh.

7. The closure of claim 6 wherein said mesh is woven.

8. The closure of claim 6 wherein said mesh is knitted.

9. The closure of claim 1 wherein said reinforcing means is molded in situ in said anchoring means.

10. The closure of claim 3 wherein said filament is molded in situ in said anchoring means.

11. The closure of claim 5 wherein said ribbon is molded in situ in said anchoring means.

12. The closure of claim 6 wherein said mesh is molded in situ in said anchoring means.

13. The closure of claim 1 wherein said anchoring means additionally comprises an upper surface and a filament receiving passageway, said reinforcing means being located between said upper surface and said filament receiving passageway, said filament extending through said filament receiving passageway, said upper surface being arranged to engage the interior of said vessel or lumen contiguous with the opening therein.

14. The closure of claim 2 wherein said anchoring means additionally comprises an upper surface and a filament receiving passageway, said reinforcing means being located between said upper surface and said filament receiving passageway, said filament extending through said filament receiving passageway, said upper surface being arranged to engage the interior of said vessel or lumen contiguous with the opening therein.

15. The closure of claim 13 wherein said reinforcing means is molded in situ in said anchoring means.

16. The closure of claim 14 wherein said reinforcing means is molded in situ in said anchoring means.

* * * * *